United States Patent [19]

Eljamal et al.

[11] Patent Number: 6,136,346
[45] Date of Patent: *Oct. 24, 2000

[54] POWDERED PHARMACEUTICAL FORMULATIONS HAVING IMPROVED DISPERSIBILITY

[75] Inventors: Mohammad Eljamal, Tripoli, Lebanon; John S. Patton, San Carlos, Calif.; Linda Foster, Mountain View, Calif.; Robert M. Platz, Half Moon Bay, Calif.

[73] Assignee: Inhale Therapeutic Systems, San Carlos, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/945,872
[22] PCT Filed: Apr. 15, 1996
[86] PCT No.: PCT/US96/05265
  § 371 Date: Mar. 17, 1998
  § 102(e) Date: Mar. 17, 1998
[87] PCT Pub. No.: WO96/32096

PCT Pub. Date: Oct. 17, 1996

Related U.S. Application Data

[63] Continuation-in-part of application No. 08/423,568, Apr. 14, 1995, abandoned.
[51] Int. Cl.$^7$ ........................................... A61K 9/14
[52] U.S. Cl. ........................ 424/488; 424/489; 424/490; 424/491; 424/499; 514/951; 514/952
[58] Field of Search ..................... 424/489, 490, 424/491, 499, 43, 488; 514/951, 952

[56] References Cited

U.S. PATENT DOCUMENTS 5,354,562 10/1994 Platz et al. .............................. 424/489
5,354,934 10/1994 Pitt et al. ..................................... 514/8

*Primary Examiner*—Michael A. Williamson
*Attorney, Agent, or Firm*—Susan T. Evans; Felissa H. Cagan; Stephen L. Hurst

[57] ABSTRACT

Dispersibility of a respirable powder, administrable by inhalation, is increased by including a pharmaceutically acceptable water-soluble polypeptide.

16 Claims, 6 Drawing Sheets

POWDERED PHARMACEUTICAL FORMULATIONS HAVING IMPROVED DISPERSIBILITY

CROSS-REFERENCE TO RELATED APPLICATIONS

This application is a 371 of PCT/US96/05265 filed Apr. 15, 1996 which is a continuation-in-part of U.S. patent application 08/423,568, filed Apr. 14, 1995, now abandoned.

FIELD OF THE INVENTION

This invention relates to powdered pharmaceutical compositions that exhibit improved dispersibility for inhalation therapy, to processes for preparing such compositions and to methods for treating certain disease states using such compositions.

BACKGROUND OF THE INVENTION

Over the years, certain drugs have been sold in compositions suitable for forming a drug dispersion for oral inhalation (pulmonary delivery) to treat various conditions in humans. Such pulmonary drug delivery compositions are designed to be delivered by inhalation of a drug dispersion by the patient so that the active drug within the dispersion can reach the lung. It has been found that certain drugs delivered to the lung are readily absorbed through the alveolar region directly into blood circulation. Pulmonary delivery is particularly promising for the delivery of proteins and polypeptides which are difficult to deliver by other routes of administration. Such pulmonary delivery can be effective both for systemic delivery and for localized delivery to treat diseases of the lungs.

Pulmonary drug delivery can itself be achieved by different approaches, including liquid nebulizers, aerosol-based metered dose inhalers (MDI's), and dry powder dispersion devices. Aerosol-based MDI's are losing favor because they rely on the use of chlorofluorocarbons (CFC's), which are being banned because of their adverse effect on the ozone layer. Dry powder dispersion devices, which do not rely on CFC aerosol technology, are promising for delivering drugs that may be readily formulated as dry powders, particularly proteins and polypeptides. Many otherwise labile proteins and polypeptides may be stably stored as lyophilized or spray-dried powders by themselves or in combination with suitable powder carriers. The ability to deliver proteins and polypeptides as dry powders, however, is problematic in certain respects. The dosage of many protein and polypeptide drugs is often critical so it is necessary that any dry powder delivery system be able to accurately, precisely, and reliably deliver the intended amount of drug. Moreover, many proteins and polypeptides are quite expensive, typically being many times more costly than conventional drugs on a per-dose basis. Thus, the ability to efficiently deliver the dry powders with a minimal loss of drug is critical. It is also important that the powder be readily dispersible prior to inhalation by the patient in order to assure adequate distribution and systemic absorption.

A particularly promising approach for the pulmonary delivery of dry powder drugs utilizes a hand-held device with a hand pump for providing a source of pressurized gas. The pressurized gas is abruptly released through a powder dispersion device, such as a venturi nozzle, and the dispersed powder made available for patient inhalation. While advantageous in many respects, such hand-held devices are problematic in a number of other respects. The particles being delivered are less than 10 μm in size, usually in the range from 1 μm to 5 μm, making powder handling and dispersion more difficult than are larger particles. The problems are exacerbated by the relatively small volumes of pressurized gas, which are available using hand-actuated pumps. In particular, venturi dispersion devices are unsuitable for difficult-to-disperse powders when only small volumes of pressurized gas are available. Another requirement for hand-held and other powder delivery devices is efficiency. It is important that the concentration of drug in the bolus of gas be relatively high to reduce the number of breaths required to achieve a total dosage. The ability to achieve both adequate dispersion and small dispersed volumes is a significant technical challenge that requires in part that each unit dosage of the powdered composition be readily and reliably dispersible.

OBJECTS OF THE INVENTION

An object of this invention is to provide a powdered pharmaceutical composition containing a drug suitable for pulmonary delivery that exhibits improved dispersibility over compositions known in the art and thus more reliable pulmonary delivery of the drug.

A further object of this invention is to provide a powdered pharmaceutical composition containing a drug suitable for pulmonary delivery that provides the amount of drug from a unit dosage form accurately, precisely and reliably.

A further object of this invention is to provide a powdered pharmaceutical composition containing a drug suitable for pulmonary delivery that exhibits the efficient delivery of drug with minimal loss per unit dosage form.

A further object of this invention is to provide a highly dispersible powdered pharmaceutical formulation containing nucleic acid plasmids (particularly a cationic lipid:DNA complex or recombinant viral particles having the desired DNA) suitable for pulmonary delivery.

A further object of this invention is to provide a process for preparing a powdered pharmaceutical composition containing a drug suitable for pulmonary delivery, which composition shows improved dispersibility over compositions known in the art.

A further object of this invention is to provide a method for treating a subject having a condition susceptible to treatment by inhalation, particularly oral inhalation, which method comprises administering the composition of this invention that exhibits improved dispersibility.

Other objects of this invention will be apparent to one of ordinary skill in the art upon reading the full specification and claims of this patent application.

SUMMARY OF THE INVENTION

One aspect of this invention is a dispersible dry power composition that is suitable for administration to a subject by inhalation, and that comprises a pharmaceutically-acceptable excipient, a therapeutically effective amount of an active agent suitable for treating a condition susceptible to treatment by oral inhalation, and a dispersibility-enhancing amount of a pharmaceutically acceptable polypeptide, e.g., HSA. Alternatively, an aspect of this invention can be viewed as an improvement over existing powdered pharmaceutical compositions suitable for inhalation therapy, in that the improvement comprises the presence of a dispersibility-enhancing amount of a pharmaceutically acceptable polypeptide in the powdered pharmaceutical composition.

Another aspect of this invention is a method of administering a therapeutically effective amount of a powdered composition of this invention to a human subject in need thereof by dispersing said powdered composition as an aerosol into a chamber having a delivery outlet suitable for inhalation therapy, e.g., a mouthpiece and having said subject inhale, preferably orally, said dispersed powder into the subject's lungs.

Another aspect of this invention is an improvement in a process for preparing a respirable powdered pharmaceutical composition. In a process for preparing a respirable powdered pharmaceutical composition by (a) foroeing a homogeneous aqueous composition comprising water, a pharmaceutically acceptable excipient and an active agent suitable for treating a disease state by inhalation, (b) removing the water from the aqueous composition to form a solid and (c) transforming the resulting solid into a respirable powdered pharmaceutical composition, the improvement of this invention comprises adding a water-soluble, physiologically-acceptable protein (e.g., HSA) to the aqueous composition in an amount sufficient to enhance the dispersibility of the resulting respirable powdered pharmaceutical composition.

Another, more specific, aspect of this invention is a method for preparing a spray-dried, dispersible powdered pharmaceutical composition that comprises spray drying a homogeneous aqueous mixture comprising water, a pharmaceutically acceptable excipient, an active agent suitable for treating a disease state by inhalation, and a dispersibility-enhancing amount of a physiologically acceptable, water-soluble protein under conditions sufficient to provide a dispersible powdered pharmaceutical composition having a particle size less than about ten microns. Alternatively, this aspect may be viewed as an improvement in a method preparing a spray-dried, dispersible, powdered pharmaceutical composition by spray drying a homogeneous aqueous mixture comprising water, a pharmaceutically acceptable excipient and an active agent suitable for treating a disease state by inhalation under conditions sufficient to provide a dispersible powder, wherein the improvement comprises including a dispersibility-enhancing amount of a physiologically acceptable, water-soluble protein in the aqueous mixture.

DEFINITIONS

In interpreting the claims to the various aspects of this invention, there are several important definitions that should be considered.

The term "powder" or "powdered" refers to a composition that consists of finely dispersed solid particles that are relatively free flowing and capable of being dispersed in an inhalation device and subsequently inhaled by a subject so that the particles reach the lungs to permit penetration into the alveoli. Thus, the powder is administrable by inhalation therapy and is said to be "respirable" and suitable for pulmonary delivery. In general, the average particle size is less than about 10 microns ($\mu$m) in diameter and the particle shapes may be irregular, uniform or mixed. Preferably the average particle size is less than about 7.5 $\mu$m and more preferably less than about 5.0 $\mu$m. Usually the particle size distribution is between about 0.1 $\mu$m and about 5 $\mu$m in diameter, particularly about 2 $\mu$m to about 5 $\mu$m.

The term "dry" means that the powder composition has a moisture content such that the particles are readily dispersible in an inhalation device to form an aerosol. This moisture content is generally below about 10% by weight (% w) water, usually below about 5% w and preferably less than about 3% w.

The term "dispersibility" means the degree to which a powder composition can be dispersed (i.e. suspended) in a current of air so that the dispersed particles can be respired or inhaled into the lungs of a subject. For example, a powder composition that is only 10% dispersible means that only 10% of the mass of finely-divided particles making up the composition can be suspended for oral inhalation into the lungs; 50% dispersibility means that 50% of the mass can be suspended. A standard measurement of dispersibility is described hereinafter.

The term "therapeutically effective amount" is the amount of an active agent present in the powder composition that is needed to provide the desired level of the active agent to a subject to be treated to give the anticipated physiological response. This amount is determined for each active agent on a case-by-case basis. Guidelines are given hereafter.

The term "physiologically effective amount" is that amount delivered to a subject to give the desired palliative or curative effect. This amount is specific for each active agent and its ultimately approved dosage level. Guidelines are given hereafter.

The term "pharmaceutically acceptable" refers to an excipient, whether a carrier or the protein used to improve dispersibility, that can be taken into the lungs with no significant adverse toxicological effects on the lungs.

DETAILED DESCRIPTION AND PREFERRED EMBODIMENTS

The present invention is based, at least in part, on the discovery that the dispersibility of a respirable powder, administrable by inhalation, is increased by including a pharmaceutically-acceptable, water-soluble polypeptide in the composition. In the preparation of powdered drug compositions for inhalation delivery, it is difficult to ensure a consistently high level of dispersibility of the compositions. It is advantageous to have a high level of dispersibility so that a greater percentage of the active agent in a unit dosage will enter a subject's lungs. It is also important to maximize the dispersibility so that less drug is lost per inhalation. For example, if only 50% of the particles making up the powder composition are dispersed, then 50% of the composition (and thus active agent) will remain undispersed and unused. This represents a significant amount of lost active agent and means that the manufacturer must take this loss into account to ensure sufficient active agent is included for delivery to a subject. Where the cost of the active agent is high, this can mean significant extra costs for the manufacturer. The present invention addresses the problem of lost active agent through improved dispersibility.

COMPOSITIONS OF THE INVENTION

One aspect of this invention is a dispersible dry power composition suitable for administration to a subject by inhalation, particularly oral inhalation, which composition comprises a pharmaceutically-acceptable excipient, a therapeutically effective amount of an active agent suitable for treating a condition susceptible to treatment by oral inhalation, and a dispersibility-enhancing amount of a pharmaceutically acceptable polypeptide. Alternatively, an aspect of this invention can be viewed as an improvement over existing powdered pharmaceutical compositions suitable for inhalation therapy, in that the improvement comprises the presence of a dispersibility-enhancing amount of a pharmaceutically acceptable polypeptide in the powdered pharmaceutical composition.

The component of the improved composition that is a pharmaceutically-acceptable excipient includes any of the standard carbohydrate and amino acid carriers that are known in the art to be useful excipients for inhalation therapy, either alone or in combination. These excipients are generally relatively free-flowing particulate solids, do not thicken or polymerize upon contact with water, are toxicologically innocuous when inhaled as a dispersed powder and do not significantly interact with the active agent in a manner that adversely affects the desired physiological action of the agent. Carbohydrate excipients that are particularly useful in this regard include the mono and polysaccharides. Representative monosaccharides include carbohydrate excipients such as dextrose (anhydrous and the monohydrate; also referred to as glucose and glucose monohydrate), galactose, mannitol, D-mannose, sorbitol, sorbose and the like. Monosaccharides are readily publicly available; for example, dextrose is available from companies such as Mallinckrodt, Inc., Corn Products Co., CPC (UK) Ltd., and/or others. Mannitol and sorbitol are available from companies such as ICI Americas, Inc., McKesson Chemical Co., Merck & Co., Atlas Chemical Industries (UK) Ltd., and/or others. Representative disaccharides, such as lactose, maltose, sucrose, trehalose and the like, can be obtained from companies such as McKesson Chemical Co., Aldrich Chemical Co., Inc., Great Western Sugar Co., and/or others. Representative trisaccharides include those such as raffinose and the like that are readily available from commercial sources. Other carbohydrate excipients include cyclodextrins such as 2-hydroxypropyl-β-cyclodextrin.

Suitable amino acid excipients include any of the naturally occurring amino acids that form a powder under standard pharmaceutical processing techniques and include the non-polar (hydrophobic) amino acids and polar (uncharged, positively charged and negatively charged) amino acids, such amino acids are of pharmaceutical grade and are generally regarded as safe (GRAS) by the U.S. Food and Drug Administration. Representative examples of non-polar amino acids include alanine, isoleucine, leucine, methionine, phenylalanine, proline, tryptophan and valine. Representative examples of polar, uncharged amino acids include cystine, glycine, glutamine, serine, threonine, and tyrosine. Representative examples of polar, positively charged amino acids include arginine, histidine and lysine. Representative examples of negatively charged amino acids include aspartic acid and glutamic acid. Of these, glycine is preferred. These amino acids are generally available from commercial sources that provide pharmaceutical-grade products such as the Aldrich Chemical Company, Inc., Milwaukee, Wis. or Sigma Chemical Company, St. Louis, Mo.

It is to be understood that suitable excipients include mixtures of one or more carbohydrates with one or more amino acids. Generally, the combination may exhibit a ratio of about 100:1 to about 1:100 parts by weight of a suitable carbohydrate to part by weight of a suitable amino acid, preferably such ratio will be between about 5:1 to about 1:5, more preferably 1:1. A particularly useful combination of this type if the combination of mannitol with glycine.

The amount of excipient that is useful in the composition of this invention is an amount that serves to uniformly distribute the active agent throughout the composition so that it can be uniformly dispersed when it is to be delivered to a subject in need thereof. It must also serve to dilute the active agent to a concentration at which the active agent can provide the desired beneficial palliative or curative results while at the same time minimizing any adverse side effects that might occur from too high a concentration. Thus, for an active agent that has high physiological activity, more of the excipient will be employed. On the other hand, for an active agent that exhibits a lower physiological activity a lesser quantity of the excipient will be employed. In general, the amount of excipient in the composition will be between about 50% weight (w) and 99.9% w. of the total composition, but because the active agent used in the composition of this invention generally have a high physiological activity, the amount of excipient will be between about 95–99.9%. For active agents that have a particularly high physiological activity, the amount will be between about 98.0% and about 99.9% w.

The component of the composition that is an active agent includes any agent that is useful for treating a human subject by inhalation therapy. Administration of the active agent exhibits a beneficial effect on the subject in that there is a palliative or curative affect on the subject's condition. Thus, the subject may be suffering from bronchial asthma or related corticosteroid-responsive bronchospastic states, hay fever, an inflamed condition, endometriosis, prostatic cancer, a bacterial infection, viral infection, or the like. In addition, the subject may be suffering from a condition that would require the administration of a nucleic acid complex of DNA or RNA material for gene therapy treatment or a treatment of a condition responsive to treatment by an interferon such as hepatitis B and C, Hairy Cell Leukemia, chronic hepatitis Non A, Non B/C, Kaposis Sarcoma, multiple sclerosis, chronic granulomatous disease, and the like. Thus, the types of active agents suitable for use in the composition include steroids (e.g. dexamethasone, triamcinolone, beclomethasone, beclomethasone dipropionate, fluocinolone, fluocinonide, flunisolide, flunisolide hemihydrate, and the like), bronchodilators (e.g. adrenalin, isoproterenol, metaproterenol, terbutaline and its salts, isoetharine, albuterol and its salts, pirbuterol and its salts, bitolterate, and the like), mast cell inhibitors (cromolyn sodium, and the like), antibiotics (e.g. pentamidine), low molecular weight polypeptides such as LHRH and its derivatives (LHRH, nafarelin, goserelin, leuprolide, and the like), high molecular weight polypeptides such as interferon or rhu IL-1 receptor, and the like. Also an active agent that is an RNA or DNA sequence that is useful for gene therapy may be employed as part of the composition of this invention. Generally the amount of active agent present in the composition will vary between about 0.1% w to about 50% w., preferably from about 0.1% w. to about 5% w. and most preferably from about 0.1% w. to about 2% weight.

In the composition of this invention useful for providing gene therapy, the active agent is an appropriate nucleic acid complex (i.e., an RNA or DNA sequence) that can be incorporated at the cellular level by administration to the lung. In general, the nucleic acid complex is a DNA associated with an appropriate cationic lipid vesicle that promotes transfection at the cellular level or in an appropriate replication deficient recombinant virus that promotes transfection at the cellular level. Representative DNA plasmids include pCMVβ (available from Genzyme Corp., Framingham, Mass.), pCMV-β-gal (a CMV promoter linked to the *E. coli* Lac-Z gene, which codes for the enzyme β-galactosidase). Representative lipids that promote transfection include DMRIE (dimyristyloxypropyl-3-dimethyl-hydroxyethyl ammonium), DOPE (dioleoyl phosphatidylethanolamine), DOTMA (N-[1-(2,3-Dioleyloxy)Propyl[-N,N,N-Trimethylammonium chloride), and the like. Such lipids may be used alone or in combination, for example, combinations of DOTMA with DOPE or DMRIE with DOPE. The nucleic acid/lipid combination is prepared by methods explained hereinafter. A more detailed explanation is set forth in Example 3. Representative replication deficient transfection viruses include the adenovirus Ad2-CMV-LacZ-2 (Genzyme Corp., Framingham, Mass.).

DOTMA is prepared in accordance with the procedure set forth in an article by Phillip L. Felgner, et al entitled "Lipofection: A highly efficient, lipid-mediated DNA-transfection procedure," Proc. Natl. Acad. Sci. USA, 84, 7413–7417, November 1987, Biochemistry. The liposome preparation is set forth in the same article as is the general method for preparing a Lipid-DNA complex that can be adjusted to be suitable for the DNA useful in this invention. DOTMA, referred to commercially as LIPOFECTIN™ is available from Bethesda Research Laboratories (BRL), Bethesda, Md. DMRIE and DOPE are available from Vical Corporation, San Diego, Calif.

The dispersing agent useful in the composition, method and process of this invention and that provides improved dispersibility is a pharmaceutically-acceptable, water-soluble, polypeptide. For purposes of this application, polypeptide is meant to encompass both naturally occurring proteins and artificially constructed polypeptides in which individual amino acid units are linked together through the standard peptide amide bond (the carboxyl group of one and the amino group of another). The dispersing agent is one that can be taken into the lungs of a patient in need thereof but will have no adverse toxicological effects at the levels used. While it is preferable that the dispersing agent be an inactive agent, it is part of this invention to include agents that may have some inherent activity of their own as long as such activity is not antithetical to the utility of the overall composition. The dispersing agent is characterized in having a molecular weight between about 1,000 and about 200,000.

Molecular weight in this context is the standard dictionary definition, which is the sum of the atomic weights of all the atoms in a molecule. This is also referred to as the formula weight. For proteins, the molecular weight may vary slightly with the method used to measure it. The methods that can be used are those well known in the art and may be based on chemical composition, number-average or weight average methods. These include the methods based on amino acid analysis, osmotic pressure measurements, sedimentation analysis, light scattering, molecular-inclusion chromatography, or SDS-gel electrophoresis (e.g., see Chapter 7 of "Biochemistry" by Albert L. Lehniger, Second Edition, 1975, published by Worth Publishers, Inc.). Others may also be used. While there may be variations in results among these methods, they are generally of a minor nature.

An example of an agent having a low molecular weight is a polyalanine having a molecular weight of about 1000. Other polypeptides in that molecular weight range which are physiologically acceptable but inactive can also be prepared. Molecules that have a molecular weight in the range of about 3000 to 6000 are also useful. If a material is used that has inherent activity of its own, it is used at levels such that the inherent activity does not interfere adversely with the activity of the active agent. Another example representative of the proteins useful in this invention include α-lactalbumin, a constituent of milk having a molecular weight of about 14,200. Another example of a representative dispersing agent is trypsinogen, which has a molecular weight of about 24,000. A dispersing agent that is particularly preferred is human serum albumin (HSA), which has a molecular weight of about 69,000 (the value is given as about 69,000 in the Merck Index, Eleventh Edition and as 68,500 in Lehniger, Second edition). Preferably the molecular weight of the protein dispersing agent is from about 1000 to about 100,000, particularly from about 1,000 to about 70,000 and more particularly about 69,000, i.e., HSA.

The amount of dispersing agent present in the composition of this invention may vary from about 1% w. to about 15% w., preferably from about 3% w. to about 8% w. and more preferably from about 3% w. to about 5% w.

In addition to the excipient of a carbohydrate, amino acid or mixtures thereof, the active agent and the protein dispersing agent, the composition of this invention may contain other pharmaceutically-acceptable excipients that may be used to stabilize the composition or make it more compatible with the unit dosage form from which it is delivered. Such excipients include, for example, buffers such as citrate, phosphate or acetate.

The composition of this invention will be delivered from a unit dosage receptacle containing an amount that will be sufficient to provide the desired physiological effect upon inhalation by a subject in need thereof. The amount will be dispersed in a chamber that has an internal volume sufficient to capture substantially all of the powder dispersion resulting from the unit dosage receptacle. Usually the volume of the chamber will be from about 50 ml to about 1000 ml, preferably from about 100 ml to about 750 ml. Thus, the unit dosage amount will be from about 2 mg of powder to about 20 mg of powder preferably about 4 mg to about 10 mg of powder per unit dosage. About 5 mg per unit dosage is quite effective. The preferred unit dosage receptacle is a blister pack, generally provided as a series of blister pack strips. The general process for preparing such blister packs or blister pack strips is generally known to one of skill in the art from such publications as Remington's Pharmaceutical Sciences (18th Edition) or other similar publications. The volume of such dosage form receptacle to accommodate the needed amount of powder of this invention will be about 1 ml to about 30 ml, preferably about 2 ml to about 10 ml.

ADMINISTRATION OF COMPOSITIONS OF THIS INVENTION

Another aspect of this invention is a method of administering a therapeutically effective amount of a powdered composition of this invention to a human subject in need thereof by dispersing said powdered composition as an aerosol into a chamber having a delivery outlet suitable for inhalation therapy, e.g., a mouthpiece and having said subject inhale, preferably orally, said dispersed powder into the subject's lungs. Generally this is accomplished in accordance with the method and apparatus described in U.S. patent application Ser. No. 08/309,691, filed Sep. 21, 1994, entitled "Method and Apparatus For Dispersion of Dry Powdered Medicaments" by Smith, Burr, Etter, Axford, Lyons and Platz, the entirety of which application is incorporated herein by reference. A further description of an apparatus useful for carrying out the method of this invention is found in U.S. patent applications Ser. Nos. 07/910,049 and 08/207/472, both of which are incorporated herein by reference.

Generally the method comprises aerosolizing a powdered composition of this invention contained in a unit dosage receptacle having an access surface wherein aerosolization is achieved by inserting a powder inlet end of a feed tube through a penetration in the access surface and flowing a high velocity gas stream past an outlet end of the feed tube so that substantially all powder in the receptacle is fluidized, drawn axially through the feed tube and dispersed in the high velocity gas stream to form an aerosol in a chamber. Further details may be obtained by reading said patent application Ser. No. 309,691 and by using a device as discussed hereinafter. In practice, a preferred unit dosage of powdered composition of this invention of about 4 mg to about 10 mg is subjected to conditions discussed hereinafter to aerosolize the powder so that a standing cloud or aerosol dispersion is created in a suitable chamber preferably of about 100 ml to 750 ml and a subject then orally inhales the dispersion into the subjects lungs.

PROCESS FOR PREPARING COMPOSITIONS OF THE INVENTION

Another aspect of this invention is an improvement in a process for preparing a respirable powdered pharmaceutical composition. In a process for preparing a respirable powdered pharmaceutical composition by (a) forming a homogeneous aqueous composition comprising water, a pharmaceutically acceptable excipient and an active agent suitable for treating a disease state by inhalation, (b) removing the water from the aqueous composition to form a solid and (c) transforming the resulting solid into a respirable powdered pharmaceutical composition, the improvement of this invention comprises adding a water-soluble, physiologically-acceptable protein to the aqueous composition in an amount sufficient to enhance the dispersibility of the resulting respirable powdered pharmaceutical composition.

Thus it can be seen that the improvement of adding the water-soluble, physiologically-acceptable protein to the aqueous composition prior to removing the water and forming the powdered pharmaceutical composition can apply to any of the processes used to make the dispersible powdered compositions of this invention. For example, the improvement applies to a process wherein the aqueous composition is lyophilized under standard lyophilizing conditions to remove the water and the resulting solid composition is transformed into a respirable, powdered pharmaceutical composition by comminuting the solid in some way such as ball-milling or jet-milling to obtain a particle size which is respirable and suitable for oral inhalation therapy. Generally that particle size will be less than 10 microns, preferably less than 5 microns. Alternatively, the improvement is equally applicable to a method of spray drying an aqueous composition to form a dispersible powdered pharmaceutical composition.

The components of the aqueous mixture are defined and set forth in the above paragraphs and the relative amounts desired in the resulting respirable pharmaceutical composition are set forth above as well.

In the preparation of the aqueous mixture for use in the process of the art and the improvement which is part of this invention, a solution or stable suspension is formed by dissolving or suspending the suitable excipient, the active agent and the physiologically acceptable, water-soluble protein in water. The order in which the components are added is not of major significance, and while the homogenous mixture may be a solution or suspension, it is preferably a solution. The proportion of the components in the aqueous mixture is consistent with the proportions that are desired in the resulting powdered composition. In general, the concentration of the materials is given in the table indicating below:

TABLE I

Suitable Aqueous Compositions

|  | Range mg/100 ml | Preferred range mg/100 ml |
|---|---|---|
| Excipient | 15–700 | 500–700 |
| Active agent | 15–700 | 15–200 |
| Protein | 7.5–110 | 20–40 |

Usually it is sufficient to prepare the aqueous mixture at temperatures that are above the freezing point of water but below a temperature which will adversely affect the activity of the active agents or the stability of the water-soluble protein which is part of the improvement of this invention. Generally the temperature will be between about 20–30° C., preferably at ambient temperatures. The pH of the solution can be adjusted by including an appropriate buffering material which will be appropriate for the desired stability of the active agent and protein. This pH will generally be in the neutral range of about pH 6–8, preferably about 7. Suitable buffering compositions can include a citrate-base buffer, phosphate base buffer or an acetate-base buffer. Other excipients may be included in the aqueous composition which would enhance the stability or the suspendability of the mixtures not a solution. Generally the aqueous solution is formed simply by mixing the appropriate concentrations of materials in water with stirring until all the materials are dissolved or dispersed and suspended in the water.

As noted before the improvement of the invention applies to a process where the solution or suspension is formed and the water is removed and the resulting solids are then transformed into a powdered composition. If the water removal and transformation to a powder can take place in a spray drying environment which allows those two steps to take place at the same time or can take place in a two-step process such as evaporation of the water under conditions that will not adversely affect the water-soluble protein or the active agent and then comminuting under conditions that will similarly not adversely affect the active agent or the effectiveness of the protein. If a two-step process is employed, it is generally preferable to lyophilize the aqueous composition in order to minimize any adverse affects on the active ingredient. Lyophilization is a freeze-drying process in which water is sublimed from the composition after it is frozen. The particular advantages of the lyophilization process are that biologicals and pharmaceuticals that are relatively unstable in aqueous solution can be dried without elevated temperatures (thereby eliminating the adverse thermal affects) and then stored in the dry state where there are few stability problems. Once it is decided that the material will be comminuted it may be done so in any manner that is appropriate but which will retain the activity in the material. In general the comminution or particle size reduction embraces a wide variety of operations that will reduce the solids obtained by lyophilization to a size which is suitable to oral administration. Generally the particle size will need to be less than 10 microns in order to be taken into the lungs and be effective. The comminution may be done in stages and may be done using any of the processes known in the art for this process. Examples are shown in Chapter 88 of *Remington's Pharmaceutical Sciences* 18th *Edition* at pages 1615–1632.

Another, more specific, aspect of this invention is a method for preparing a spray-dried, dispersible powdered pharmaceutical composition that comprises spray drying a homogeneous aqueous mixture comprising water, a pharmaceutically acceptable excipient, an active agent suitable for treating a disease state by inhalation and a dispersibility-enhancing amount of a physiologically acceptable, water-soluble protein under conditions sufficient to provide a dispersible powdered pharmaceutical composition having a particle size less than about ten microns. Alternatively, this aspect may be viewed as an improvement in a method preparing a spray-dried, dispersible, powdered pharmaceutical composition by spray drying a homogeneous aqueous mixture comprising water, a pharmaceutically acceptable excipient and an active agent suitable for treating a disease state by inhalation under conditions sufficient to provide a dispersible powder, wherein the improvement comprises including a dispersibility-enhancing amount of a physiologically acceptable, water-soluble protein in the aqueous mixture.

In general, it is preferable to prepare the compositions of this inventions through the use of a spray dryer. This method generally consists of bringing together a highly dispersed liquid, which is the aqueous composition defined above, and a sufficient volume of hot air to produce evaporation and drying of the liquid droplets. The feed liquid may be solution, slurry, emulsion, gel or paste provided the feed is capable of being atomized. Preferably a solution is employed. In general the feed is sprayed into a current of warm filtered air that evaporates the water and conveys the dried product to a collector. The spent air is then exhausted with the moisture. While, in general, the resulting spray-dried powdered particles are homogenous, approximately spherical in shape, nearly uniform in size and frequently are hollow, the improvement of this invention seems to result in a mixture of particles that are more irregular in shape. In some way this irregularity may contribute to the greater dispersibility of the compositions of this invention. A further discussion of spray drying can be found in Chapter 89 of *Remington's* at pages 1646–47. It is found that the process of this invention works particularly well using a Buchi spray dryer apparatus having a serial number of 190. Generally the inlet temperature and the outlet temperature of the spray dry equipment are not critical but will be of such a level to provide the desired particle size and to result in a product that has the desired activity of the active agent. The inlet temperature thus may be between temperatures of 80° C. to about 150° C. with the outlet temperature being at temperatures of about 50° C. to 100° C. Preferably these temperatures will be from 90° C. to 120° C. for inlet and from 60° C. to 90° C. for the outlet. The flow rate which is used in the spray drying equipment generally will be about 3 ml per minute to about 5 ml per minute. The atomizer air flow rate will vary between values of 700 LPH (liters per hour) to about 800 LPH. Secondary drying not needed, but may be employed.

By following the general process teachings above one obtains a composition having the desired particle size and dispersibility characteristics to respirable and suitable for pulmonary delivery to a subject in need thereof. In general the average particle size is less than about 10 microns in diameters with particle shapes that are irregular, uniform or a mixture of shapes. Preferably, the average particle size is less than about 7.5 microns and more preferably less than about 5 microns in diameter. Usually the particle size distribution is between about 0.1 micron and about 5 microns, particularly about 2 microns to about 5 microns.

The particle size distribution (PSD) of the powder composition of this invention is measured using an Horiba CAPA-700 centrifugal sedimentation particle size analyzer. Usually, as measurement is taken on approximately 5 mg of powder that is suspended in approximately 5 ml of Sedisperse A-11 (Micromeritics, Norcross, Ga.) and briefly sonicated before analysis. The instrument is configured to measure a particle size range of 0.40 to 10 $\mu$m in diameter and the centrifuge is operated at 2000 rpm. The particle size distribution of the powder is characterized by mass median diameter (MMD) and determining the percentage of the particles with a MMD less than 5.2 $\mu$m. The values obtained are the mean of 2 replicate measurements. Generally, the powder composition of this invention exhibits a mean particle size distribution of 2 to 3 microns. Particles of less than 5 $\mu$min size can be delivered to the deep lung for systemic circulation.

DISPERSIBILITY DETERMINATION

To determine the dispersibility of a composition of this invention as compared to other compositions, one can use a standard test for quantifying the deliverable dose of a unit dosage form by aerosolizing a powder composition, collecting the aerosolized composition and measuring the delivered material using the equipment and procedure as described hereinafter.

A high level of dispersibility leads to a high percentage of delivered dose of a composition of this invention. Delivered dose is a key parameter in the success of a powdered composition. It is a measure of the efficiency by which a composition is delivered by a dry powder pulmonary inhaler device to (1) extract the test powder from a dosage receptacle such as a blister package, (2) aerosolize that powder into a "standing cloud" of fine particles in an aerosol chamber, (3) deliver those fine particles through the mouthpiece of the device during a test inhalation. The dose delivered with each formation tested is generally determined as follows using a device wherein a single blister pack, filled with approximately 5 mg of powder, is loaded into the device. The device is actuated, suspending the powder into the device's aerosol chamber. The "standing cloud" of fine particles is then drawn from the chamber at an airflow rate of 30 L/min for 2.5 seconds (1.25 L inspired volume) and the sample collected on a suitable filter, a polyvinylidene fluoride membrane filter with a 0.65 $\mu$m pore size is particularly useful. The sampling airflow pattern is controlled by an automatic timer and operated to simulate a patient's slow deep inspiration. The overall efficiency (delivered dose) and percent of the powder left in the blister pack after actuation is determined gravimetrically by weighing the powder on the filter and the amount of powder left in the blister pack. This process may be visualized as follows:

5 mg. powder in blister pkg. → suspended by device into chamber → "inhaled" onto filter → filter weighted _ % left in blister     _ % left in device     _ % collected on filter The calculation of dispersibility is as follows:

1. Total mass of powdered composition in a unit dosage (e.g., a 5 mg blister pack).

2. Total mass of powdered composition aerosolized in a unit dosage and collected on filter (e.g., 2.5 mg).

3. Dispersibility is defined as the mass of powder collected on filter divided by the mass of powder in the blister expressed as a percent (e.g., 2.5÷5=50%).

Equipment that is suitable (with minor modifications) for use in determining dispersibility is described in PCT application published as International Patent Number WO 93/00951, published Jan. 21, 1993 entitled Method and Device For Aerosolized Medicaments by John S. Patton. That application in its entirety is incorporated herein by reference.

The dispersibility is determined using a system as described hereinafter or a system that may incorporate portions of equipment described in the above WO93/00951 publication in combination with the system described hereinafter. Each system is also adaptable for administering a composition of this invention to a subject in need thereof.

Figure 1:
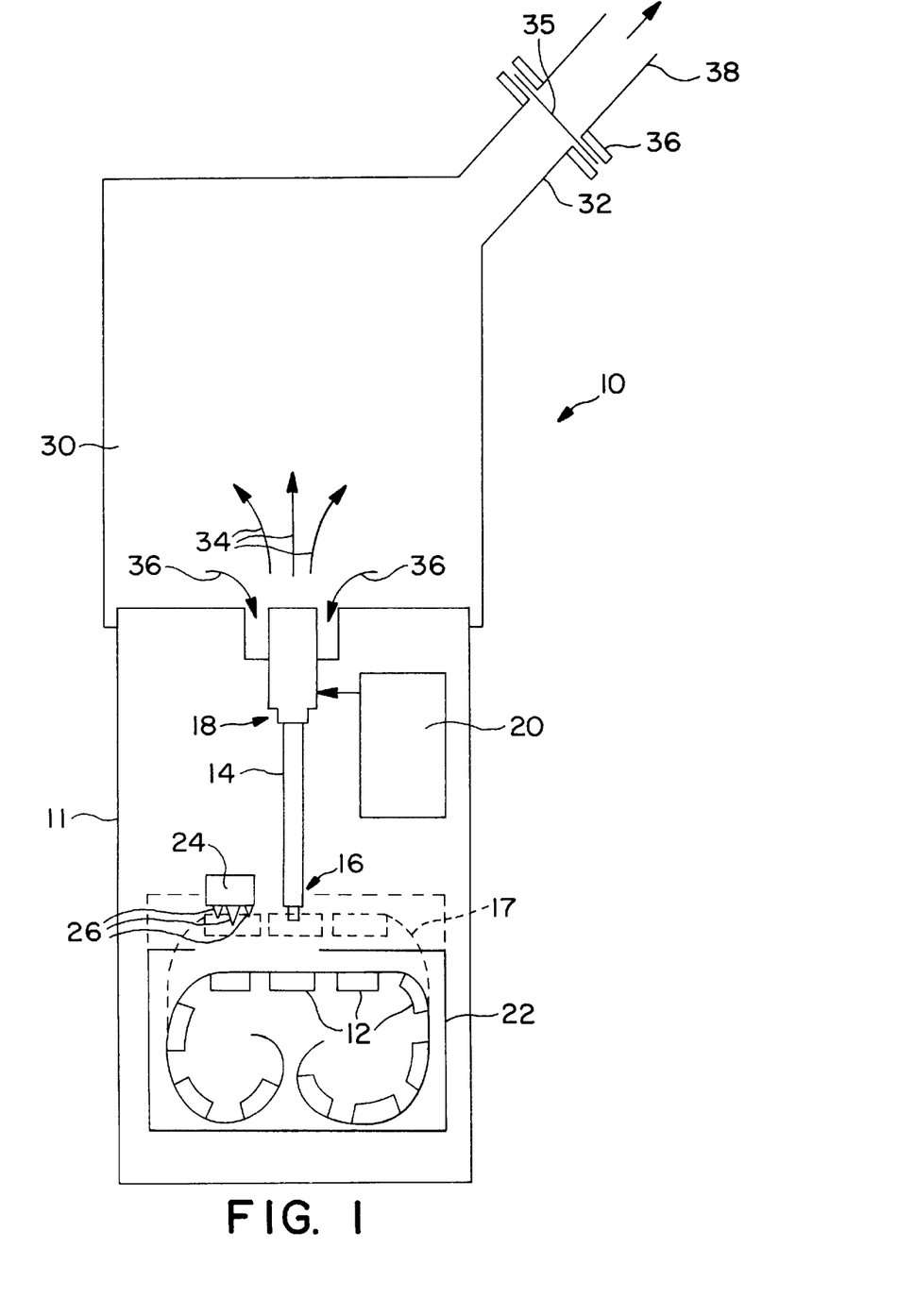
FIG. 1 is a cross-sectional view of a system for dispersing a powdered medicament.

Referring now to FIG. 1, a system 10 for dispersing a powder medicament from a plurality of receptacles 12 will be described. As illustrated, receptacles 12 are in a continuous web comprising individual wells covered by a puncturable lid or access surface, typically a metal foil or other conventional laminate. Each receptacle will include a precise dosage of the powdered medicament to be delivered. The amount of powder in each individual receptacle will usually be in the range from about 2 mg to 20 mg, more usually being from 4 mg to 10 mg, preferably being about 5 mg. The manufacture of such "blister pack strips" is well known in the pharmaceutical packaging art and need not be described further.

Although illustrated with cartridge 22, it will be appreciated that the powder dispersion systems could also be constructed to receive single dosage packages carrying only one receptacle. In such a case, the user would insert the package so that the receptacle was properly oriented relative to the feed tube 16. Necessary punctures in the access surface of the receptacle could be made manually prior to insertion or could be preformed and exposed by peeling away a cover. Multiple receptacle packages could also be provided where the package is inserted into the device at different orientations in order to selectively expose individual receptacles to the feed tube. A variety of design options is available when the user inserts a single receptacle prior to each use.

The system 10 further comprises a feed tube 14 having an inlet end 16 and an outlet end 18. A pressurized gas source 20 is also provided within the base enclosure 11 and is connected to the feed tube 14 to provide a high velocity gas stream, as will be described in greater detail in connection with FIG. 2.

The receptacles 12 will be mounted within a base enclosure 11 to reciprocate relative to the inlet end 16 of feed tube 14. Preferably, the strip of receptacles 12 will be mounted within a cartridge 22 which is reciprocally mounted in the base enclosure 11, while the feed tube 14 is fixedly mounted within the base enclosure. In this way, the receptacles 12 may be sequentially advanced past a fluidization location (defined by the inlet end 16 of feed tube 14) within the cartridge 22, with the receptacle at the dispersion or fluidization location being brought proximate the inlet end 16 of the feed tube to permit emptying of its powdered contents, as described in more detail hereinafter. Both reciprocation of the cartridge 22 and advance of the receptacles 12 within the cartridge may be accomplished manually by the user. Alternatively, a mechanism may be provided within the base enclosure 11 for simultaneously reciprocating the cartridge 22 and advancing the strip of receptacles 12, either as part of a manual advance mechanism or as part of an electrical- or battery-powered mechanism.

Figure 3:
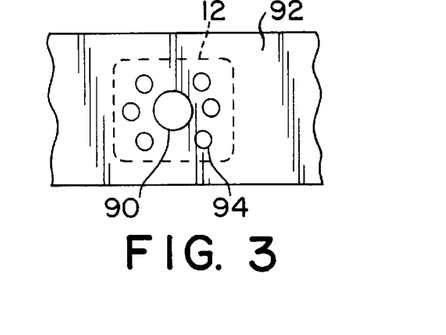
FIG. 3 shows a top view of a puncturable lid.

Penetrations will be formed in the lid of the strip of receptacles 12 by a punch mechanism 24. As illustrated, the punch mechanism 24 will be fixedly mounted within the base enclosure 11 and will include a plurality of sharpened penetration elements 26 disposed to contact and penetrate the puncturable lid 92 (FIG. 3) of the receptacles 12 when the cartridge 22 is reciprocated, as illustrated in broken line 17 in FIG. 1. The punch mechanism 24 will be located to contact a receptacle 12 which is located one station prior to the feed tube 14. Thus, each receptacle 12 will be punched immediately prior to being advanced to the fluidization location.

It will be appreciated that a wide variety of mechanisms can be provided for punching holes within the lid of each receptacle and for bringing the receptacle into proximity with the feed tube 14. For example, the cartridge 22 could be held stationary within the base enclosure 11 while each of the feed tube 14 and punch mechanism 24 be reciprocated, either together or separately. Alternatively, the inlet end 16 of the feed tube 14 could be configured to be self-penetrating. In the latter case, the desired pattern of penetrations would be formed in the puncturable lid of the receptacle 12 at the same time that the inlet end is inserted into the interior of the receptacle. The present invention is not limited to any particular puncturing and advance mechanisms which might be employed.

The gas source 20 will provide a volume of high-pressure air or other gas to the feed tube 14 in order to draw powder from the receptacles 12 and disperse the powder into a flowing gas stream. The gas source will provide gas at a relatively high pressure, usually being sufficient to provide for sonic flow past the outlet end 18 of the feed tube 14, typically being above 15 psig, and preferably being in the range from 20 psig to 100 psig. The volume of high pressure gas (which relates directly to the amount of stored energy) provided by gas source 20 will be sufficient to entrain air through the feed tube which in turn draws fluidization air into the receptacle to fluidize and extract the expected weight of powdered medicament from the receptacle 12, typically being in the range from about 2 ml to 100 ml (measured at standard temperature and pressure), usually being in the range from about 3 ml to 25 ml. The specific manner in which the high-pressure gas is flowed past the outlet end 18 of feed tube 14 will be described in greater detail in connection with FIG. 2.

Gas source 20 may be in the form of a manual pump, an electric pump, a high-pressure gas cylinder, or the like. The construction of manual pumps in hand-held powder dispersion devices is described in the patent and technical literature. See, e.g., WP90/07351. The construction of electric gas pumps, gas cylinder supplies, and two-fluid systems is also well within the skill and the art. See for example WO93/00951.

The gas dispersion system 10 further includes a plume capture chamber 30 which is disposed over the outlet end 18 of feed tube 14 in order to capture powder released from the tube. The plume chamber 30 will include a mouthpiece 32 at its distal end and will have an internal volume sufficient to capture substantially all of the powder dispersion which is delivered from the feed tube 14. Usually, the volume will be in the range from 50 ml to 1000 ml, preferably from 100 ml to 750 ml. The chamber 30 will also include an ambient air inlet (not shown), typically a tangential inlet as described in co-pending application Ser. No. 07/910,048, the full disclosure of which is incorporated herein by reference.

At the mouthpiece 32 there is shown a flange 36 and exit line 38. A suitable filter paper 35 is inserted in flange 34 between mouthpiece 32 and exit line 36.

If the apparatus is to be used for administration to a human subject, the subject would simply place the mouthpiece 32 in his or her mouth and inhale to contents of chamber 30 after the aerosol is formed.

In operation, to measure dispersibility, the powder dispersion will be introduced into the plume capture chamber 30, as illustrated by arrows 34. A vacuum is drawn on exit line 38 to bring air and the dispersed particles in the plume chamber through the mouthpiece 32 and filter 35 and optionally back through an annular lumen in the feed tube 14, as indicated by arrows 36 and as will be described in more detail in connection with FIG. 2. Such recycling of air from the plume capture chamber 30 as the fluidization gas greatly reduces the total volume of new gas being introduced to the system. The only new gas introduced will be from the gas source 20. After the entire contents of a receptacle 12 have been dispersed and captured within the plume chamber 30 (the mouthpiece optionally will have an anti-backflow valve to prevent leakage, the vacuum will bring the entire aerosolized dose through the mouthpiece 32 and filter 35 and continue inhalation to draw ambient air through the chamber to sweep any residual medicament which may be present. A particularly useful filter 35 which is used in this case is a low protein binding filter 47 mm in diameter having a 0.65 micron pore size of polyvinylidene fluoride (PVDF), available from Milapore Manufacturing Company and having a trade name of DURAPORE (catalog number DVPP 047000). The filter 35 is held in a custom filter holder and the line 38 is attached to a vacuum source. The filter paper is weighed using a Metier AT 261 balance or equivalent in a 2 ml polypropylene tube. The standing cloud of fine particles is drawn from the plume chamber through the filter with the air flow pattern being controlled by an automatic timer (Eagle Model CX300).

Figure 2:
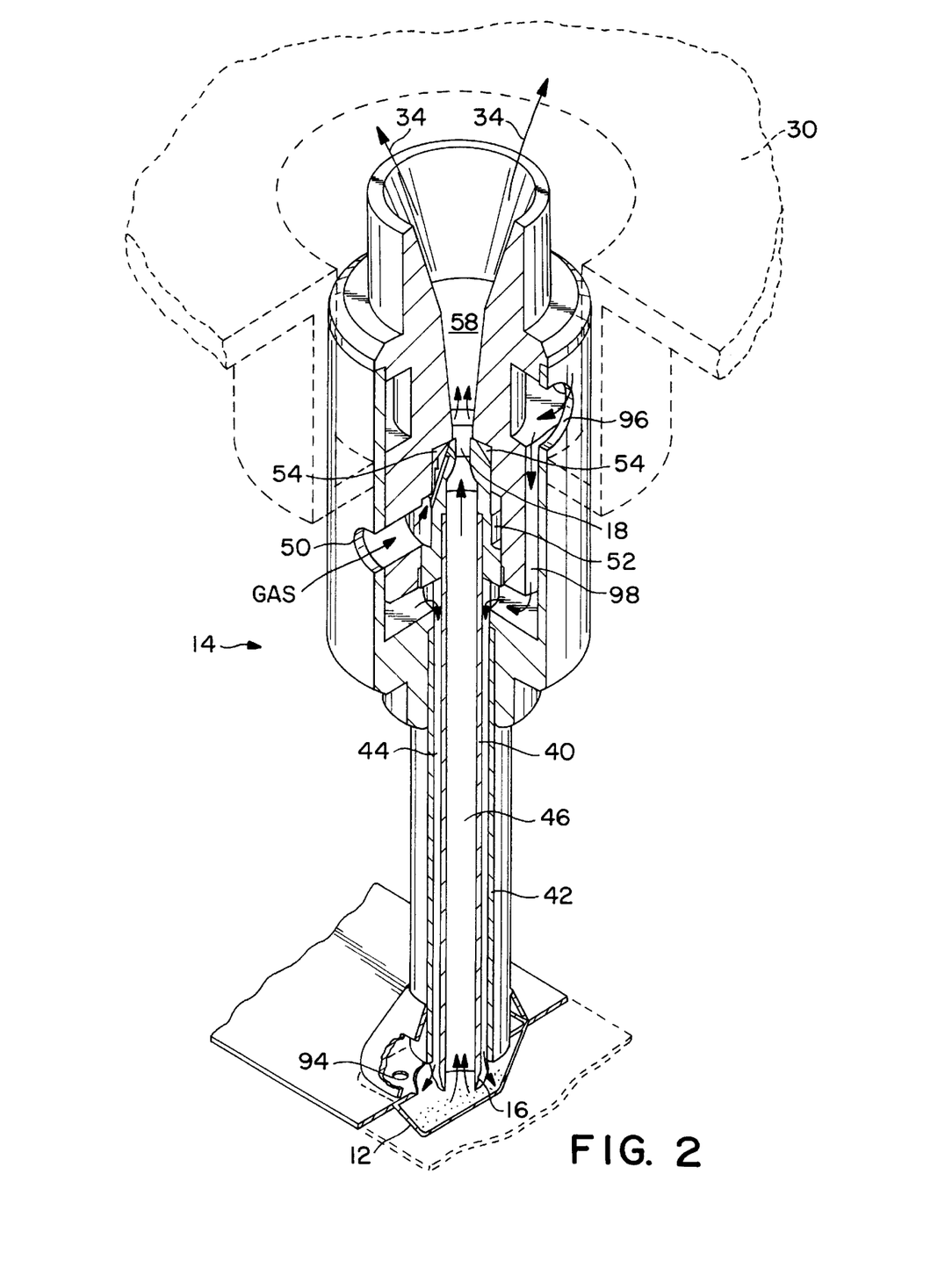
FIG. 2 is a cut-away view of a feed tube assembly for the system for dispersing a powdered medicament.

Referring now to FIG. 2, the feed tube assembly 14 includes an inner tubular member 40 which defines the inlet end 16 at its distal end and an outer coaxial tube member 42 which defines an annular lumen 44 for passing return air from chamber 30 back to the receptacle 12, as described in more detail hereinafter.

Lumen 46 of the inner tubular member 40 extends from the inlet end 16 to the outlet end 18 where a throat or constriction is formed. The throat or constriction is not necessary for operation of the feed tube assembly 14, but it is the diameter and area of the outlet end of the lumen 46, in this case defined by the constriction which determines the performance characteristics of the feed tube, as described in more detail hereinafter. Dispersion gas from gas source 20 enters the feed tube assembly 14 through a port 50 connected to an annular plenum 52. The annular plenum 52, in turn, is connected to a pair of gas conduits 54 which direct converging gas streams into the flow path defined by lumen 46 of the inner tubular member 40. The angle at which the gas conduits 54 are oriented is chosen to provide a proper balance between the magnitude of the flow velocity induced in the powder stream drawn through lumen 46 and the magnitude of the shear forces which break up agglomerates in the powder as they pass from the outlet end 18 into an expansion section 58.

Figure 4A:
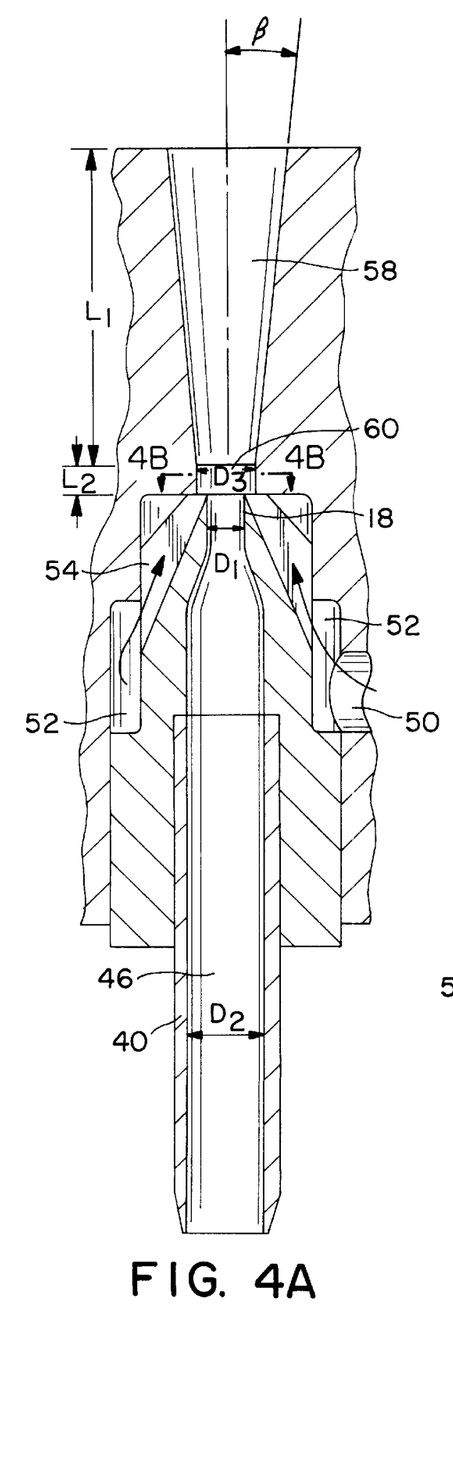
FIGS. 4A, 4B and 4C are detailed views of the throat assembly of the system for dispersing a powdered medicament.

The diameter D1 (FIG. 4A) of the throat 18 of the feed tube lumen 46 will typically be in the range from 2 mm to 7 mm, preferably being in the range from 3 mm to 5 mm. In the illustrated embodiment, the diameter D2 of the upstream portion of lumen 46 is greater than D1, typically being from 2.5 mm to 10 mm. The lumen 46, however, could have a uniform diameter along its entire length equal to the outlet end diameter D1, although such a construction would be less preferred.

The outlet end 18 opens into expansion or diffusion section 58 which has a length L in the range from 0.5 cm to 10 cm, preferably from 1 cm to 5 cm. A dispersion region 60 having a uniform diameter D3 in a length L2 is provided immediately at the outlet end 18. The diameter D3 is shown to be slightly larger than outlet diameter D1, but this is not necessary. The exemplary diameter D3 is typically in the range from 2 mm to 10 mm. The length L2 is in the range from 1 mm to 10 mm.

Figure 4B:
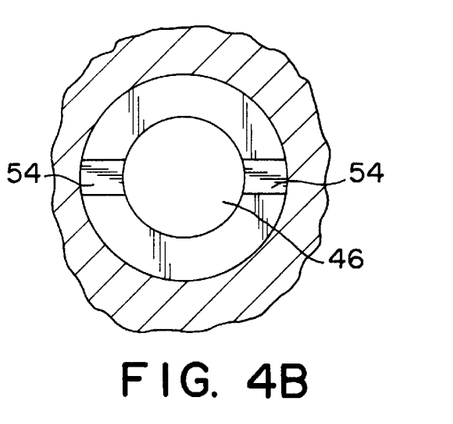
Figure 4C:
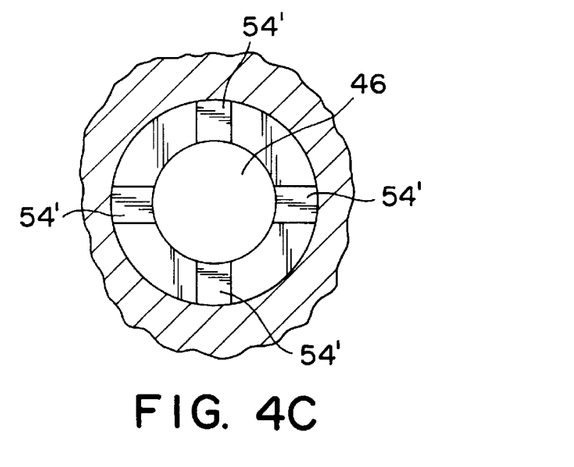

In the illustrated embodiment, a pair of gas conduits 54 are shown, as illustrated in FIG. 4B. It would also be possible to provide three or four separate inlets 54. as illustrated in FIG. 4C. Other configurations will also be usable including a continuous annular aperture, as described in connection with FIG. 6.

Figure 5:
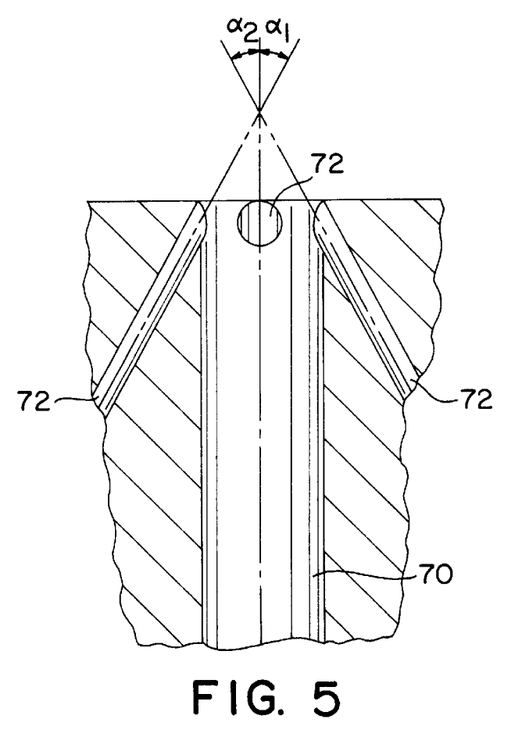
FIG. 5 is a cross-sectional view of the high velocity gas conduits around a feed tube lumen.

Referring now to FIG. 5, high-velocity gas conduits 72 are arranged around the throat of a feed tube lumen 70 at angles $\alpha_1$ $\alpha_2$, which will usually but not necessarily be equal. The angles $\alpha$ are important to achieving both adequate mass transfer of powder from the receptacle and adequate agglomerate breakup as the powder enters the dispersion region immediately downstream from the outlet orifices of the conduits 72. The angles $\alpha$ will be in the range from 40° to 80°, preferably being from 45° to 70°.

Figure 6:
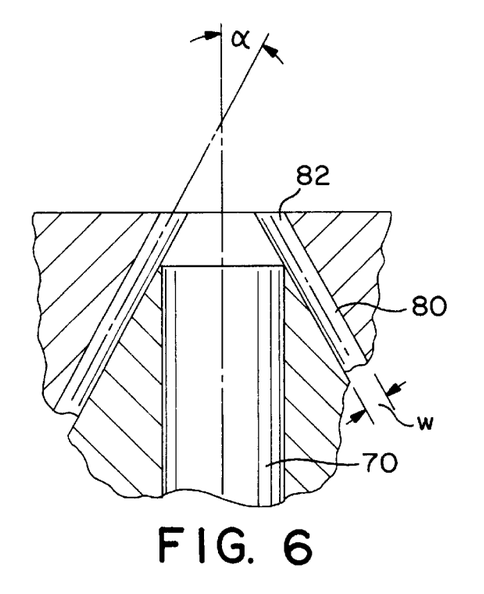
FIG. 6 is a cross-sectional view of the high velocity gas conduits wherein they are formed as a simple conical plenum.

It will be appreciated that the high-velocity gas lumens 72, as illustrated in FIG. 5, may be formed as a single conical plenum 80 terminating in an annular aperture 82, as illustrated in FIG. 6. The angle of convergence $\alpha$ will generally be within the range set forth above for $\alpha_n$ in Table 1, and the total area of the annular lumen 82 will generally be within the total area for the high-velocity gas lumens $A_1$, also set forth in Table 1. Typically, the conical plenum 80 will have a width w in the range from about 0.05 mm to 0.1 mm.

Referring again to FIG. 2, the feed tube assembly 14 operates by inserting the inlet end 16 of the inner tube member 40 into a central aperture 90 (FIG. 3) punched into access surface 92 over a receptacle 12. The central aperture 90 will be surrounded by spaced-apart apertures 94 (usually six) which allow for the entry of fluidizing and sweeping air as powder is withdrawn through the inner tube member 40. In a preferred aspect of the present invention, at least a portion of the fluidizing air will be returned through the annular lumen 44 via a port 96 at the bottom of the interior of the plume chamber 30. Such return flow of air or gas from the plume chamber 30 passes through an annular plenum 98 from the port 96 into the annular lumen 44. Optionally, a rubber flange or skirt (not shown) may be provided to prevent loss of return air from the lumen 44 to the receptacle 12. The transfer of displacement air from the plume chamber 30 helps contain the plume of dispersed powder within the plume chamber since it limits the amount of air which is expelled through the mouthpiece 32 or other opening in the chamber.

Introduction of the inlet end 16 of inner tube member 40 of the feed tube assembly 14 into the receptacle 12 is particularly advantageous since it facilitates substantially complete removal of powder from the interior of receptacle. Such complete removal is further enhanced by the entry of displacement air through the space-apart apertures 94, which creates a flow of air which can sweep powder from all corners of the receptacle into the dispersion lumen 46.

Although the foregoing invention has been described in some detail by way of illustration and example, for purposes of clarity of understanding, it will be obvious that certain changes and modification may be practiced within the scope of the appended claims.

In preparing samples for the dispersibility determination there are certain materials and equipment that is needed to do the determination. A sample blister package having a unit dosage form of a composition to be measured as a standard is obtained and a blister package of the same variety containing the powdered composition to be compared are set up.

To determine the degree of dispersion of the composition, a clean filter is weighed on the appropriate balance and placed in the filter flange 35 (or housing) to securely hold the filter in place. After appropriate adjustments are made to the rate of flow to the air on the flow meter the timer is set for the appropriate interval, generally about 5 seconds and the filter in the filter housing is attached to the holder in the aerosol chamber of the device. The blister pack is then punctured and the exposed blister pack is loaded into the device. The device is then actuated for the time set the vacuum is started and the process can be repeated for 1 or 2 times to collect more than one puff of the dispersed powder on the filter. Thereafter the filter housing is disassembled, the filter is retrieved and weighed to determine the amount of material collected on the filter. The calculations for the dispersibility are shown hereinbefore.

The following preparations and examples are given to further explain the details of representative aspects of the invention but are not intended to limit the scope of the claims in any way.

PREPARATION 1

This preparation sets forth a method for preparing a composition of a carbohydrate excipient, mannitol, and a cationic lipid suitable for use in transfecting cells, a combination of DOTMA with DOPE. The dispersibility characteristics of the liposome/mannitol composition prepared without a suitable physiologically acceptable protein to improve dispersibility.

Twenty-five μMoles (33 mg) of a cationic lipid comprising DOTMA:DOPE (1:1 by weight—from Megabios Co.) and 675 mg of mannitol was dissolved in 100 ml of deionized water. The resulting solution was processed into a spray-dried powder using a Buchi-190 spray drier using the following spray drying parameters:

solution feed rate 5.8 ml/min

Inlet/outlet temperature 137° C./73° C.

Atomizer air flow rate 800 LPH*

*LPH=liters per hour

The powder yield was only 6% of theory and the resulting powder was too sticky to determine its dispersibility.

PREPARATION 2

This description sets forth a standard in vitro assay that is useful to determine whether a composition will transfect cells (cytofection) with a nucleic acid complex in the composition. Transfection takes place when the complex that is introduced into the cell subsequently caused the cell to express the encoded protein.

The cell of choice (CFT1 cell line, cells obtained from the airways of cystic fibrosis patients) are placed into 96-well plates at 20,000 per well in growth medium the day before the cells were to be cytofected. Just prior to cytofection, the cells were observed and approximate confluency estimated. The freshly made material is prepared by formulating the lipid to 670 μM and the DNA to 960 μM then adding the resulting lipid formulation to the DNA. The complex is formed for 15 minutes before 100 μl of the complex is then added to the cells and cytofection is followed. Generally cytofection occurs over 6 hours before the addition of 50 μl 30% FCS-OPTIMEM. The following day, 100 μl of 10% FCS-OPTIMEM is added to each well. Assay begins 48 hours after the start of cytofection. To determine whether cytofection has taken place, the following steps are observed: the media is removed and the cells washed twice with 100 μl (PBS). A 25 μl of lysis buffer (0.15% Triton X100 in 250 μM Tris-HCI, pH 8.0) is added to each well. The plate is incubated at room temperature for 30 minutes, frozen at −70° C. for 20 minutes and thawed at room temperature for 15 minutes. The cells are broken up by carefully vortexing the plate for 15 seconds then freezing the resulting plate at −70° C. for 20 minutes and thawing for another 15 minutes at room temperature. A 100 μl PBS is added to the well followed by 150 μl of CPRG substrate (1 mg chlorophenol red galactopyranoside is dissolved in 1 ml of 60 mM disodium hydrogen phosphate, pH8, containing 1 mM magnesium sulfate, 10 mM potassium chloride and 50 mM β-mercaptoethanol). The resulting composition is incubated at 37° C. for two hours until red color develops and the plate is read at 580 nm in a microplate reader. The results are then tabulated as appropriate.

EXAMPLE 1

This example describes the effect of adding a suitable physiologically-acceptable protein, HSA, to a liposome/mannitol composition to improve the dispersibility characteristics.

(A) Twenty-five μMoles (33 mg) of a cationic lipid comprising a DOTMA:DOPE (1:1 by weight—from Megabios Co.) was mixed with 675 mg of mannitol and 0.16 ml of HSA (12.5 g/50 ml—from Alpha Therapeutic) in 100 ml of deionized water. Thirty ml of the resulting 3% HSA solution was processed into a spray-dried powder in accordance with the process of part (A) of this Example under the following conditions:

solution feed rate 3 ml/min

Inlet/outlet temperature 94° C./56° C.

Atomizer flow rate 800 LPH (B) To 70 ml of the solution of part (A) of this Example, 0.15 ml of HSA was added to give a solution that was 12.4% HSA. The resulting solution was spray dried at the following conditions:

solution feed rate 3 ml/min

Inlet/outlet temperature 103° C./68° C.

Atomizer flow rate 800 LPH

The powder yield for the above process (A) was 55% of theory. The dispersibility of the powder was found to be 36±4% by using the method set forth in this specification. The powder yield for part (B), above, was 54%, and the dispersibilty was 59±4%. This shows the importance of the presence of HSA in improving the dispersibility of the liposome/mannitol composition. See Table I.

TABLE I

| Formula # | Composition HSA/Lipid/Mannitol (mg/ml) | Yield % | Dispersibility % |
|---|---|---|---|
| Prep 1 | 0.00/0.35/6.75 | 6 | — |
| Ex 1A | 0.40/0.35/6.40 | 55 | 36 ± 4 |
| Ex 1B | 0.91/0.35/6.40 | 54 | 59 ± 4 |

EXAMPLE 2

This example sets forth a composition that preserves the integrity of a representative DNA molecule while showing good dispersibility. A composition of pCMVβ in Tris/Mannitol/HSA solution (7.5 mg/ml solids) was spray-dried using a Buchi-190 spray drier under the following conditions:

solution feed rate 4.3 ml/min
Inlet/outlet temperature 120° C./70° C.
Atomizer flow rate 800 LPH The resulting powder flowed easily and was reconstituted in de-ionized water and was run in gel electrophoresis (1.3% agrose in 0.5×TBE plus 0.5 μg/ml ethidium bromide, 100 volts for 4 hours). Unprocessed pCMVβ was also run in the same gel. Similar bands were observed for both the processed and unprocessed pCMVβ in the gel electrophoresis indicating the integrity of the DNA is preserved. While the dispersibility of the composition appeared good and integrity of the DNA is preserved, the composition showed no transfection activity in the cytofection assay of Preparation 2.

EXAMPLE 3

This example sets forth a process for preparing a composition of this invention that is useful for pulmonary delivery for gene therapy and the composition itself. In the composition, the excipient is mannitol, the physiologically acceptable protein is HSA and the active agent a combination of DMRIE:DOPE (50/50 w/w) with the DNA, pCMV-β-gal from Genzyme Corp.

In preparing the composition of this invention, 5 mg of DMRIE:DOPE (50/50 3.75 mMole) is dissolved in 2.4 ml filtered and deionized water and vortexed at full speed for 1 minute to generate 1.56 mM cationic lipid solution. Two ml of water are mixed with 0.86 ml of the resulting aqueous suspension to make 670 μM.

To prepare the DNA/liposome composition, 0.145 ml of DNA, which is supplied as a 4.26 mg/ml dispersion, and 1 mM Tris buffer pH 8, and 1.9 ml of 1 mM Tris buffer pH 8 are combined to make a 960 μM mixture. Using the aqueous formulations prepared above, liquid formulations of the following lipid:DNA (μM:μM) ratios were prepared 0:0, 0:6.9, 20.9:12.8, 10.4:12.8, 5.2:12.8, 10.4:6.9, 5.2:6.9, 2.6:6.9, 0.4:3.5, 5.2:3.5 and 2.6:3.5). These were prepared in 25 ml of Tris/mannitol/HSA buffer having a pH of 8. Aliquots of 1 ml were drawn from each aqueous composition then refrigerated and were used as controls to investigate the effect of powder processing on the transfection activity of the complex.

The liquid formulations were then spray dried in a Buchi-190 spray drier. The following conditions were maintained during processing:

Inlet temperature between 115–125° C.
Outlet temperature between 70–85° C.
Atomizer flow rate 700 liters per hour (LPH) compressed air
Solution feed rate 3.8 ml/min
Secondary drying 10 min. at 60–75° C.

Aliquots of the powder were assayed for transfection activity using the cytofection assay described in Preparation 2 and were compared to liquid formulation controls which had been drawn from the liquid formulations prior to spray drying and to freshly made transfecting formulations which were prepared about 15 minutes prior to the cytofection test.

The results show that by forming the lipid DNA into a powder of this composition, the transfection activity of the complex as compared to the liquid formulation is nearly as high.

EXAMPLE 4

This example sets forth a process for preparing a composition of this invention that is useful for pulmonary delivery for gene therapy and the composition itself. In the composition, the excipient is glycine or glycine with mannitol, the dispersing agent is HSA and the active agent a combination of DMRIE:DOPE with DNA as shown in Example 2. The liposomes are first prepared by dissolving 5 mg vial of DMRIE:DOPE (50:50, 3.75 μMole cationic lipid DMRIE) in 2.0 ml filtered and deionized water and vortexing at full speed for 1 minute to generate 1.56 mM cationic lipid. This is diluted to 4 ml with water to make 940 μM and sonicated for 5 minutes then put on ice for storage. The DNA is prepared by dispersing 0.5 ml of the DNA material, which is supplied as 4.26 mg per ml dispersion and 1 mM Tris buffer at pH 8.0 in 6.75 ml water to make 960 μM that also is put on ice for storage.

The lipid:DNA complex was then prepared (A) in glycine/HSA and (B) in glycine/mannitol/HSA solutions without any buffer. Formulations of the following lipid:DNA (μM:μM) ratios were prepared. 20:20, 20:15, 10:15, 10:10 and 10:5. These were all prepared in 25 ml solutions. Aliquots of 1 ml were drawn then refrigerated and were used as liquid controls to investigate the effect of powder processing on the transfection activity of the complex.

Figure 7:
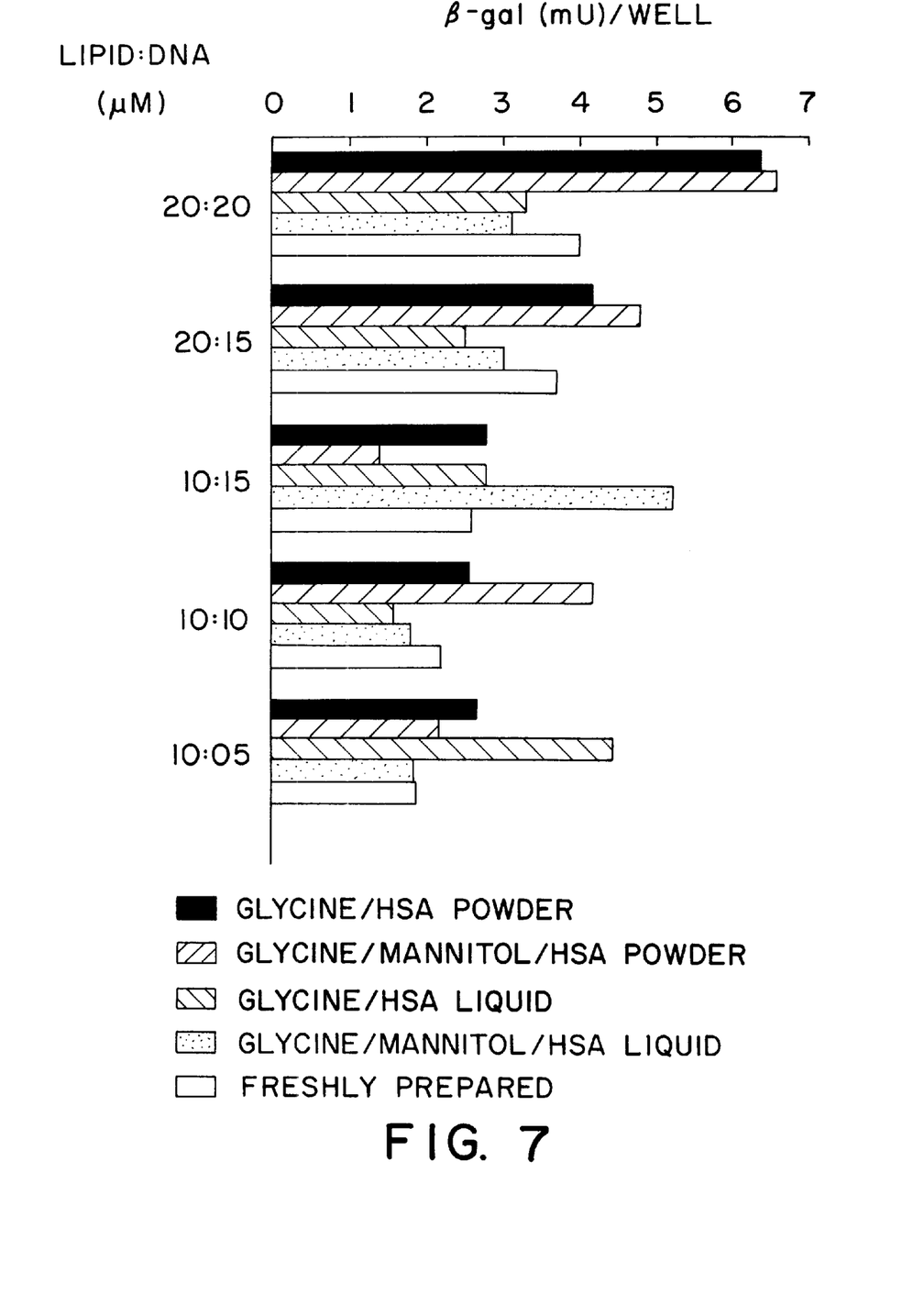
FIG. 7 shows the Transfection activity of Lipid:DNA complex in cell culture.
Figure 8:
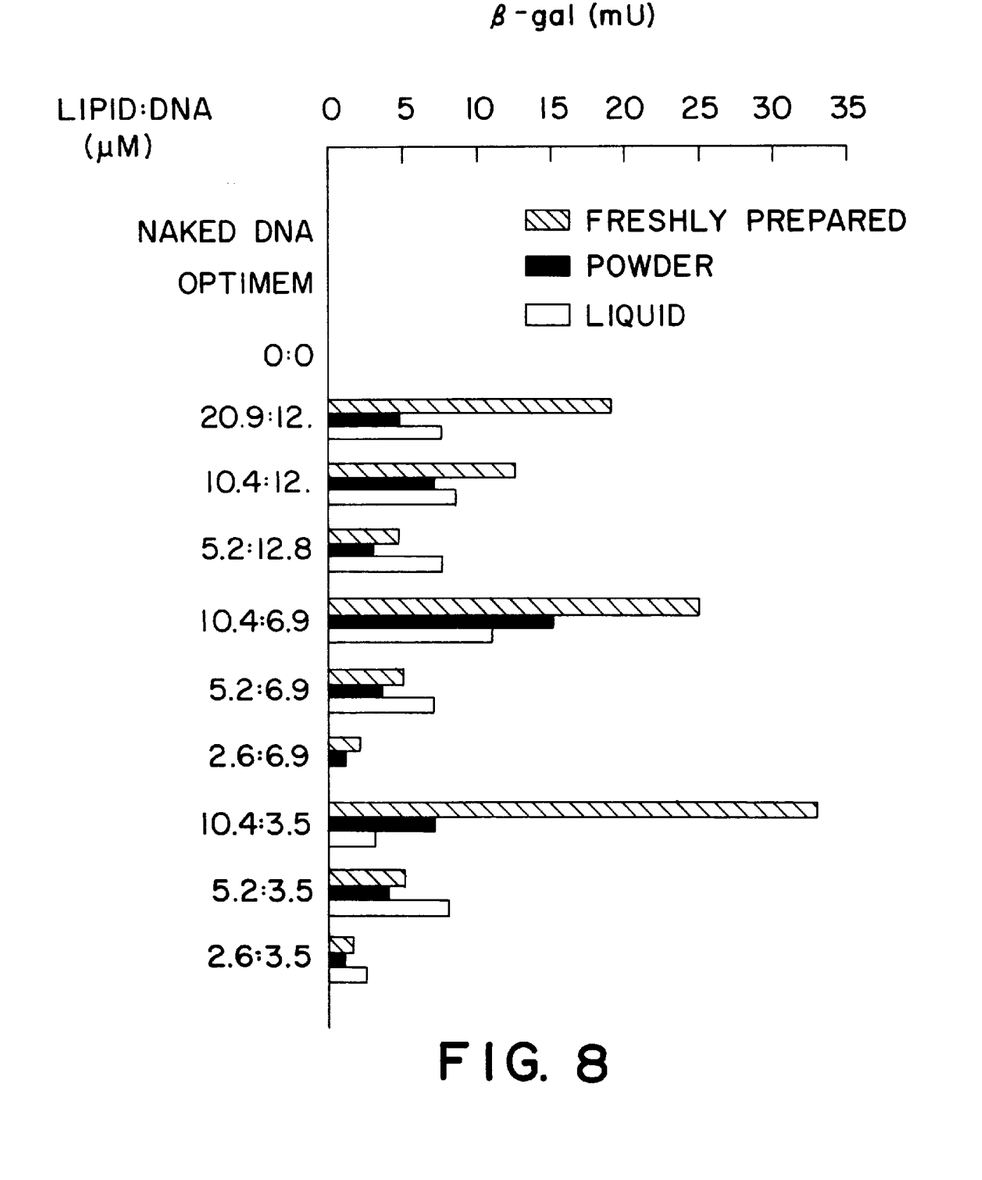
FIG. 8 shows the Transfection activity of Lipid:DNA complex in cell culture.

The liquid formulations thus prepared were spray dried in a Buchi-190 spray dryer under the following conditions during processing:

Inlet temperature between 115–125° C.
Outlet temperature between 70–85° C.
Atomizer flow rate 700–800 LPH compressed air
Solution feed rate 3.8 ml/min Aliquots of the liquid formulations prior to spray drying and of the resulting spray-dried powdered compositions of this invention were assayed for transfection activity in vitro in accordance with the procedure of Preparation 2 and were compared to freshly-prepared lipid/DNA samples with similar concentration ratios liquid formulations. A comparison of β-gal expression in vitro (CFT, cell line), the powdered composition of this invention, and the two liquid formulations (the pre spray-dried control aliquot and the freshly made material) are shown in FIGS. 7 and 8. The powders were reconstituted in double distilled de-ionized water. The transfection activities of liquid and powder formulations which contained the Tris buffer, were less than the freshly prepared liquid formulations (FIG. 7). In the powders, which contained no buffer, there was a 75% increase in the transfection activity of the 20:20 and 30% increase in the 20:15 as compared with the freshly prepared liquid formulations.

The measured physical parameters of the selected powders that showed superior transfection are listed in Table 2. The Glycine/HSA and GlycinelMannitol/HSA powder formulations had similar transfection activities (FIG. 7) but the glycine/HSA powders dispersed better than the Glycine/Mannitol/HSA (Table 2).

TABLE 2

Lipid: DNA Powder Physical Characteristics

| Formula Bulking | | Dipersi. (% RSD) | HORIBA | Cascade Impactor | |
|---|---|---|---|---|---|
| ratio | Material | (n = 3) | MMD* | MMAD** | % ≦ 5 μm |
| 20:20 | Glycine | 61(20) | 2.0 | 3.9 | 60 |
| 20:15 | Glycine | 64(1) | 2.0 | 2.4 | 75 |
| 20:20 | Gly/Man | 47(12) | 2.0 | 3.0 | 70 |
| 20:15 | Gly/Man | 51(12) | 2.4 | 4.1 | 60 |

*MMD: Mass Median Diameters
**MMAD: Mass Median Aerodynamic Diameters

*MMD: Mass Median Diameters
**MMAD: Mass Median Aerodynamic Diameters

EXAMPLE 5

This example sets forth certain compositions of this invention useful for gene therapy.

This example includes two sets of experiments. (A) In the first set, we investigated the effects of carbohydrate and amino acid excipients in phosphate buffer (PB), (i) Mannitol/HSA, (ii) Glycine/HSA and (iii) Mannitol/Glycine/HSA, on the infectivity of the adenovirus dry powders. (B) In the second set, we investigated the effects of buffer removal and the process outlet temperature on the infectivity. All solutions were used and stored cold (~5° C.).

(A) (i) To 4×3 ml Mannitol/HSA it was added 0.1 ml of adenovirus solution to obtain 3.2×10$^7$ iu/ml and ~60 mg/ml solids, and the fifth was used as a control with no virus. Two of the virus formula were diluted with de-ionized water to ~9 mg/ml solids. (ii) Two formulations of 6.3 ml Glycine/HSA (I) in PB plus 0.4 ml adenovirus solution were made (29 mg/ml solids, 6.3×10$^7$ iu/ml). One of them was diluted with de-ionized water to 9 mg/ml solids. (iii) Two formulations of 4.1 ml Mannitol/Glycine/HSA in PB plus 0.4 ml of virus solution were made (45.1 mg/ml solids, 8.89×10$^7$ iu/ml). One was diluted with de-ionized water to 9 mg/ml. The adenovirus solution was freshly made on the same day and was kept cold on ice.

(B) Four formulations were prepared wherein two contained 25 ml of Glycine/HSA (II) in PB plus 0.4 ml of adenovirus solution (10.5 mg/ml, 1.6×10$^7$ iu/ml) and the other two contained 25 ml of Glycine/HSA (II) in water plus 0.4 ml of adenovirus solution (8.6 mg/ml, 1.6×10$^7$ iu/ml). The adenovirus solution underwent only one freeze/thaw cycle before usage in the above preparations. It was prepared about 10 weeks prior and was stored frozen at −70° C.

These formulations were processed into powders in the Buchi-190 spray dryer according to the following parameters:

Solution feed rate: 3.5–6.0 ml/min
Inlet/Outlet temperatures: 100–140/70–90° C.
Atomize flowrate: 700–800 LPH The resulting powder was kept refrigerated. Prior to testing for β-gal expression or for virus titers the powders were reconstituted with phosphate buffered saline (PBS).

RESULTS

None of the mannitol powder formulations showed any β-gal expression in the standard 6-well test and therefore they were not tittered for virus infectivity. The Glycine/HSA (I) and Glycine/Mannitol/HSA in PB from set 1 were equal in their β-gal expression and were tittered for virus infectivity. Their titers ranged from 7 to 15% of the expected values. The particle size distribution (HORIBA), dispersibility and the aerodynamic size distribution (IMPAQ 6-stage) are listed in Table 3 for the two Glycine/HSA in PB powders.

(B) powders and 0.1 ml of the adenovirus solution (V) frozen to −70° C. were shipped on dry ice to Dr. Larry A. Couture (Genzyme, Mass.) for titer measurements (Table 4). Powders manufactured with and without the phosphate buffer retained 76–54% and 2–1.4% of their virus infectivities, respectively (Table 4). Lowering the outlet temperature by 5° C. increased the buffered formulation virus infectivity by 22% but it lowered the unbuffered one by 6%.

TABLE 3

Glycine/HSA Adenovirus Formulations

| Formula | Dipersi. | HORIBA | Cascade impactor | | % infectivity |
|---|---|---|---|---|---|
| (mg/ml) | (% RSD) | MMD | MMAD | % <5 μm | retained |
| 29 | 40(25) | 2.6 | 2.8 | 70 | 14 |
| 9 | 51(1) | 2.3 | 1.8 | 80 | 7 |

TABLE 4

Adenovirus Powders in Buffer and Without Buffer Titer Results

| Formulation | Outlet Temp. ° C. | Expected iu/ml | Measured iu/ml |
|---|---|---|---|
| V | N/A | 1.0 × 10$^9$ | 1.6 × 10$^8$ |
| Buffered | 77 | 1.0 × 10$^8$ | 5.4 × 10$^7$ |
| Buffered | 72 | 1.0 × 10$^8$ | 7.6 × 10$^7$ |
| Unbuffered | 77 | 1.0 × 10$^8$ | 2.0 × 10$^6$ |
| Unbuffered | 72 | 1.0 × 10$^8$ | 1.4 × 10$^6$ |

What is claimed is:

1. A method of preparing a spray-dried, dispersible powdered pharmaceutical composition, comprising:

spray-drying a homogeneous aqueous mixture comprising a pharmaceutically-acceptable excipient, a dispersibility-enhancing, physiologically-acceptable, water-soluble polypeptide and an active agent to obtain an aerosolizable, dispersible powder composition suitable for administration to a human subject by inhalation therapy, whereby the presence of the polypeptide in the mixture is effective to increase the dispersibility of the spray-dried powder composition over the dispersibility of the spray-drying a homogeneous aqueous mixture comprising a pharmaceutically-acceptable excipient, a dispersibility-enhancing, physiologically-acceptable, water-soluble polypeptide and an active agent to obtain an aerosolizable, dispersible powder composition suitable for administration to a human subject by inhalation therapy, whereby the presence of the polypeptide in the mixture is effective to increase the dispersibility of the spray-dried powder composition over the dispersibility of the composition prepared in the absence of said polypeptide.

2. The method of claim 1 wherein the excipient is present in an amount sufficient to provide about 50% by weight to about 99.9% by weight of the excipient in the dispersible composition.

3. The method of claim 2, wherein the polypeptide is present in an amount sufficient to provide about 1% by weight to about 15% by weight of the polypeptide in the dispersible powdered composition formed.

4. The method of claim 3 wherein the polypeptide is present in an amount sufficient to provide about 3% by weight to about 5% by weight of the polyppide in the dispersible powdered composition.

5. The method of claim 1 wherein the polypeptide is human serum albumin.

6. The method of claim 1 wherein said excipient is a carbohydrate or an amino acid.

7. The method of claim 6, wherein said excipient is a carbohydrate selected from the group consisting of monosaccharides, disaccharides, trisaccharides and polysaccharides.

8. The method of claim 7, wherein said excipient is a monosaccharide selected from the group consisting of dextrose, galactose, mannitol, D-mannose, sorbitol, and sorbose.

9. The method of claim 7, wherein said excipient is a disaccharide selected from the group consisting of lactose, maltose, sucrose, and trehalose.

10. The method of claim 6, where said excipient is a non-polar amino acid.

11. The method of claim 6, where said excipient is a polar amino acid.

12. The method of claim 10, where said amino acid is selected from the group consisting of alanine, isoleucine, leucine, methionine, phenylalanine, proline, tryptophan, and valine.

13. The method of claim 11, where said amino acid is selected from the group consisting of arginine, histidine, lysine, cystine, glycine, glutamine, serine, threonine, tyrosine, aspartic acid and glutamic acid.

14. The method of claim 1, where said dispersing agent is selected from the group consisting of polyalanine, α-lactalbumin, trypsinogen, and human serum albumin.

15. The method of claim 1, where said dispersible composition comprises particles having a size less than 10 microns.

16. A method for improving the dispersibility of a spray-dried powdered pharmaceutical composition, comprising:
(i) adding to a homogeneous aqueous mixture comprising a pharmaceutically-acceptable excipient and an active agent, a dispersibility-enhancing amount of a physiologically-acceptable, water-soluble polypeptide, and
(ii) spray-drying the mixture from step (i) to form an aerosolizable, dispersible powder composition suitable for administration to a human subject by inhalation therapy, whereby adding the polypeptide to the mixture is effective to increase the dispersibility of the resulting spray-dried powder composition over the dispersibility of such composition prepared in the absence of said polypeptide.

* * * * *

UNITED STATES PATENT AND TRADEMARK OFFICE
CERTIFICATE OF CORRECTION

PATENT NO : 6,136,346

DATED : October 24, 2000

INVENTOR(S) : Mohammad Eljamal, et al.

It is certified that error appears in the above-identified patent and that said Letters Patent are hereby corrected as shown below:

Column 22, delete lines 56-65

Signed and Sealed this

Fifteenth Day of May, 2001

Attest:

NICHOLAS P. GODICI

*Attesting Officer*      *Acting Director of the United States Patent and Trademark Office*